US006348210B1

(12) United States Patent
Gale

(10) Patent No.: US 6,348,210 B1
(45) Date of Patent: Feb. 19, 2002

(54) METHODS FOR TRANSDERMAL DRUG ADMINISTRATION

(75) Inventor: Robert Martin Gale, Los Altos, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 09/438,574

(22) Filed: Nov. 10, 1999

Related U.S. Application Data

(60) Provisional application No. 60/108,341, filed on Nov. 13, 1998.

(51) Int. Cl.⁷ .......................... A61F 13/02; A61F 13/00; A61L 15/16
(52) U.S. Cl. ........................................ 424/448; 424/449
(58) Field of Search .................................. 424/448, 449

(56) References Cited

U.S. PATENT DOCUMENTS

| | | | |
|---|---|---|---|
| 3,598,122 A | 8/1971 | Zaffaroni | 128/268 |
| 3,598,123 A | 8/1971 | Zaffaroni | 128/268 |
| 3,731,683 A | 5/1973 | Zaffaroni | 128/268 |
| 3,797,494 A | 3/1974 | Zaffaroni | 128/268 |
| 4,031,894 A | 6/1977 | Urquhart et al. | 128/268 |
| 4,201,211 A | 5/1980 | Chandrasekaran et al. | 128/268 |
| 4,286,592 A | 9/1981 | Chandrasekaran | 128/260 |
| 4,314,557 A | 2/1982 | Changrasekaran | 128/260 |
| 4,379,454 A | 4/1983 | Campbell et al. | 604/897 |
| 4,435,180 A | 3/1984 | Leeper | 604/896 |
| 4,551,490 A | 11/1985 | Doyle et al. | 524/22 |
| 4,559,222 A | 12/1985 | Enscore et al. | 424/28 |
| 4,568,343 A | 2/1986 | Leeper et al. | 604/896 |
| 4,588,580 A | 5/1986 | Gale et al. | 424/21 |
| 4,645,502 A | 2/1987 | Gale et al. | 604/896 |
| 4,698,062 A | 10/1987 | Gale et al. | 604/896 |
| 4,704,282 A | 11/1987 | Campbell et al. | 424/449 |
| 4,725,272 A | 2/1988 | Gale | 424/448 |
| 4,725,439 A | 2/1988 | Campbell et al. | 424/449 |
| 4,781,924 A | 11/1988 | Lee et al. | 424/449 |
| 4,788,062 A | 11/1988 | Gale et al. | 424/449 |
| 4,816,258 A | 3/1989 | Nedberge et al. | 424/448 |
| 4,849,226 A | 7/1989 | Gales | 424/448 |
| 4,867,982 A | 9/1989 | Campbell et al. | 424/449 |
| 4,904,475 A | 2/1990 | Gale et al. | 424/449 |
| 4,908,027 A | 3/1990 | Enscore et al. | 604/890 |
| 4,911,916 A | 3/1990 | Cleary | 424/449 |
| 4,917,895 A | 4/1990 | Lee et al. | 424/448 |
| 4,938,759 A | 7/1990 | Enscore et al. | 604/896 |
| 4,943,435 A | 7/1990 | Baker et al. | 424/448 |
| 5,004,610 A | 4/1991 | Osborne et al. | 424/448 |
| 5,059,189 A | 10/1991 | Cilento et al. | 604/307 |
| 5,312,627 A | 5/1994 | Stroppolo et al. | 424/448 |
| 5,411,740 A | 5/1995 | Lee et al. | 424/448 |
| 5,508,038 A | 4/1996 | Wang et al. | 424/448 |
| 5,635,203 A | 6/1997 | Gale et al. | 424/448 |
| 5,827,530 A | * 10/1998 | Reed et al. | |
| 6,007,837 A | * 12/1999 | Enscore et al. | |
| 6,024,974 A | * 2/2000 | Li | |

FOREIGN PATENT DOCUMENTS

EP   0 374 980 B1   6/1990   ........... A61L/15/16

\* cited by examiner

*Primary Examiner*—Thurman K. Page
*Assistant Examiner*—Isis Ghali
(74) *Attorney, Agent, or Firm*—Vandana Date

(57) ABSTRACT

Adhesive transdermal drug delivery devices may be removed and subsequently reapplied to an area of skin if the adhesive has an initial adhesive/skin bond strength sufficient to maintain said transdermal drug delivery device on the skin to which it is applied for the entire predetermined administration period; and an adhesive/skin bond strength upon replacement on the skin after removal therefrom which is adequate to retain the device on the skin for the balance of the administration period.

17 Claims, No Drawings

METHODS FOR TRANSDERMAL DRUG ADMINISTRATION

The inventor claims the benefit of the filing date of provisional application Ser. No. 60/108,341 filed Nov. 13, 1998.

FIELD OF THE INVENTION

This invention relates to methods for transdermal drug administration. More particularly, but without limitation thereto, this invention provides a greater degree of freedom in transdermal drug delivery regimens whereby transdermal drug delivery devices may be removed and subsequently reapplied to the same or other areas of non-scrotal skin.

BACKGROUND OF THE INVENTION

The transdermal route of parenteral drug delivery provides many advantages over other administrative routes. Transdermal devices for delivering a wide variety of drugs or other beneficial agents are described in U.S. Pat. Nos. 3,598,122; 3,598,123; 3,731,683; 3,797,494; 4,031,894; 4,201,211; 4,286,592; 4,314,557; 4,379,454; 4,435,180; 4,559,222; 4,568,343; 4,588,580; 4,645,502; 4,698,062; 4,704,282; 4,725,272; 4,725,439; 4,781,924; 4,788,062; 4,816,258; 4,849,226; 4,867,982; 4,904,475; 4,908,027; 4,917,895; 4,938,759; 4,943,435; 5,004,610; 5,411,740;5,635,203, and 5,827,530 which are hereby incorporated in their entirety by reference.

One problem associated with many adhesive transdermal drug delivery devices of the prior art is that they often loose their adhesive properties and loosen or fall off before the predetermined drug administration period was completed. To deal with this problem, some products were sold with adhesive overlays that could be applied on top of the device and extending beyond its original borders to keep the device in place for the remainder of the administration period. Another common approach to resolution of this problem was to use adhesives which were highly aggressive, i.e., as close to being painful to remove as possible without actually being too painful. Removal of such systems resulted in damage to the adhesive surface which made them unsuitable for reapplication.

On the other end of the spectrum, transdermal delivery devices such as those disclosed in U.S. Pat. Nos. 4,704,282; 4,725,439 and 4,867,982 noted above have been designed to be applied to sensitive skin sites such as the scrotum or breast. These devices have non-adhesive skin contacting surfaces that have a low level of tack in order to allow them to non-adhesively cling to the skin. Testoderm® transdermal testosterone represents this type of product and users were instructed that it could be removed while showering or swimming, for example, and then replaced. An improved version of Testoderm®, Testoderm® with adhesive, had thin stripes of polyisobutylene adhesive applied to about 12% of the surface of the device to assist in maintaining the device on the scrotum and this product could also be removed and replaced in the same manner as the original Testoderm® product. Neither of these products, however, could be used on non-scrotal skin.

Another attempt to overcome the re-adhesion problems is disclosed in U.S. Pat. No. 4,911,916, hereby incorporated in its entirety by reference. The device disclosed therein includes a means to restore the adhesiveness of the skin contacting surface of the device after removal from the skin. This was accomplished by adding a sufficient amount of the pressure sensitive adhesive to the drug reservoir whereby any adhesive left on the surface of the skin upon removal of the device would be replaced by adhesive diffusing from the drug reservoir to the skin contacting surface such that the device could then be replaced or repositioned on the skin without significant loss of adhesion.

The ability to remove and to reapply a transdermal drug delivery device makes it more convenient to extend the functional life of the device as shown, for example, in U.S. Pat. No. 5,827,530. Instead of being refilled while still on the patient, the device can be removed, refilled and replaced.

Various adhesives are known to the art for maintaining transdermal drug delivery devices in drug transmitting relationship with the skin or mucosa as disclosed in the above patents. Such adhesives may be formed from both cross-linked and non-crosslinked polymers including, for example, acrylates, silicones, polyurethanes, styrene-butadiene block polymers, and polyisobutylene (PIB) polymers and mixtures of the above.

It is known to provide non-crosslinked polyisobutylene (PIB) adhesives as a mixture of high molecular weight (HMW) and low molecular weight (LMW) PIBs with or without a plasticizer such as mineral oil or polybutene. In such formulations, the HMW PIB acts as an adhesive base, the LMW PIB acts as a tackifier, and a plasticizer, if present, acts to plasticize the adhesive to increase permeability of the adhesive to the drug and to modify the adhesive properties. Typical plasticizers include mineral oil, polybutene, and in some cases, such as with nicotine, the drug itself. A typical formulation of the prior art uses HMW PIB of 1.2M molecular weight LMW PIB of 35,000 molecular weight and plasticizer in a ratio of about 1:1.125:2.

It is also known to include additional tackifiers, if desired, to improve adhesive characteristics of such adhesives. PIB adhesives comprising a mixture of high, medium, and/or low molecular weight PIB's are disclosed in European Patent 0374980 and in U.S. Pat. Nos. 4,031,894, 4,559,222, 4,938,759, 5,312,627, and 5,508,038. PIB adhesive blends with butyl rubber or styrene radial or block type copolymers are disclosed in U.S. Pat. Nos. 4,551,490 and 5,059,189. The above patents are hereby incorporated in their entirety by reference.

DEFINITION OF TERMS

As used herein, the term "drug" is to be construed in its broadest sense to an any material which is intended to produce some biological, beneficial, therapeutic, or other intended effect, such as permeation enhancement, for example, on the organism to which it is applied.

As used herein, LMW PIB, refers to a PIB having a molecular weight within the range of 1,000–450,000 and HMW PIB refers to a PIB having a molecular weight within the range of 450,000–2,000,000.

As used herein, the term "predetermined administration period" refers to the period of time the transdermal delivery delay is designed to be maintained in contact with the skin of a patient to produce the desired therapeutic effect and is usually specified in the prescribing information supplied with the product.

As used herein, the term "transdermal" refers to the use of skin as a portal for the administration of drugs by topical application of the drug thereto.

SUMMARY OF THE INVENTION

According to this invention it has been discovered that transdermal drug delivery devices comprising adhesive formulations having certain adhesive properties can be successfully applied to, removed from and thereafter reapplied to non-scrotal skin without seriously degrading the adhesive properties after being removed.

Adhesive transdermal drug delivery devices may be removed and subsequently reapplied to an area of skin if the adhesive has an initial adhesive/skin bond strength sufficient to maintain said transdermal drug delivery device on the skin to which it is applied for the entire predetermined administration period; and an adhesive/skin bond strength upon replacement on the skin after removal therefrom prior to the end, if the predetermined administration period, which is adequate to retain the device on the skin for the balance of the administration period.

Accordingly, this invention relates to methods for the transdermal administration of a drug for a predetermined administration period wherein a transdermal delivery device is applied to non-scrotal skin, removed prior to the expiration of said administration period and thereafter reapplied for the balance of said administration period.

These and other aspects of the invention will become apparent to those of ordinary skill in the art in view of the detailed description that follows.

DETAILED DESCRIPTION OF THE INVENTION

I have found that certain transdermal adhesive formulations can be tailored such that they provide: (a) an adhesive/skin bond strength sufficient to maintain a transdermal drug delivery device on non-scrotal skin for the entire predetermined drug administration period; and (b) when removed from the skin prior to expiration of said time period and then replaced on the skin, an adhesive/skin bond strength sufficient to maintain the device on the skin for the balance of the predetermined time period.

The use of such adhesives makes it possible to interrupt the transdermal administration of drugs through non-scrotal skin one or more times by enabling the device to be applied to the skin, removed and thereafter reapplied to non-scrotal skin.

I believe that the decrease in adhesiveness observed when transdermal systems of the prior art were removed from and replaced on non-scrotal skin can be attributed to: (1) delamination of the device because the adhesive/skin bond strength is greater than (a) the cohesive strength of the adhesive itself or (b) the bond strength between the adhesive and an adjacent layer in the device; or (2) the adhesive/skin bond strength is higher than the cohesive strength of the skin such that a significant portion of the adhesive surface is contaminated with skin debris.

The strength of the adhesive/skin bond can be determined using an Instron® meter to measure the force of removal as is known to the art. The bond strength should be measured at least 20 minutes after application in order to allow for full bond strength to develop. I have determined that adhesives having adhesive/skin bond strengths of about 195 gm/cm when so measured are not suitable for use in transdermal devices that are to be removed and reapplied because substantially no bond strength is retained upon reapplication. I have also determined that adhesives having adhesive/skin bond strengths of about 95 gm/cm, which have adequate bond strength to be maintained on the skin for at least 24 hours, can be removed and reapplied with substantially no decrease in bond strength upon reapplication. Adhesives suitable for reapplication typically retain an adhesive/skin bond strength upon replacement on the skin after removal therefrom which is no less than 72% and preferably no less than 85% of the initial adhesive/skin bond strength.

I believe, without being limited thereto, that the surface characteristics of non-crosslinked adhesives, such as PIB adhesives, allows the material forming the adhesive surface to flow on a microscopic scale to a greater extent than crosslinked adhesives. This would allow for a greater degree of self-repair for damage that may be sustained by the adhesive surface when it is removed from the skin. Accordingly, non-cross-linked adhesives, and the PIB adhesives particularly, are preferred embodiments of this invention. However, great flexibility exists in the tailoring of the adhesive properties of all types of adhesives, including cross-linked adhesives, and the use of such cross-linked adhesives, typically the acrylate and silicone based adhesives commonly used in the transdermal drug delivery art, is within the scope of this invention, provided their adhesive properties are adjusted as defined above.

When transdermal drug delivery devices use adhesive formulations having the characteristics of this invention, the user can remove the device from non-scrotal skin when engaged in certain activities such as swimming, bathing, sun tanning or other activities in which, for one reason or another, it is desired to remove the device prior to the expiration of the entire predetermined drug administration period and then reapply the device to the same, or preferably a different skin site for the remaining useful life of the device. This has proven to be a desirable feature of a commercial product according to this invention, Testoderm TTS® which was introduced in the United States by the assignee in February 1998.

The predetermined administration periods typically vary from 16–24 hours to one week depending on the drug being administered. For example, nicotine and nitroglycerin devices are typically applied for 16–24 hours; hormone replacement, fentanyl and scopolamine are typically applied for periods in the 1–3 day range, and clonidine is applied for one week.

PIB adhesives suitable for use with this invention are known in the art as disclosed in the above cited patents. Preferably, the adhesive comprises a plasticizer such as mineral oil or polybutene, preferably in an amount ranging from 35–65 wt %. In some cases a plasticizer will not be necessary, such as when a low molecular weight PIB (1000–15000 MW) is used, or when the drug itself plasticizes the adhesive mixture.

A transdermal device usable according to this invention is disclosed in commonly owned, copending application Ser. No. 08/886,960, herein incorporated in its entirety by reference. As disclosed therein, the adhesive can be a mixture of HMW PIB/LMW PIB/Plasticizer in a ratio of 0.75–1.25/1–1.5/1.5–2.5, most preferably 1/1.25/2. The adhesive characteristics of the PIB mixture can be adjusted by varying the HMW/LMW plasticizer ratio as well as by the use of various tackifiers and other additives as is known to the art.

Also, small amounts of styrene-isoprene-styrene block copolymers or polybutene grafted acrylate adhesives (PGM) can be added to the PIB adhesive formulation. Such a PIS adhesive according to this aspect of the invention would also comprise 0–15% isoprene rubber or PGAA, 2–50% rosin tackifier, 0–50% plasticizer such as mineral oil or polybutene, with the balance of the adhesive comprising a HMW PIB, LMW PIB or mixtures thereof.

The surface area of devices according to this invention can vary from about 5 $cm^2$ to about 75 $cm^2$. A typical device, however, will have a surface area within the range of about 20–60 cm². A typical transdermal device according to this invention is conveniently fabricated as generally elliptical or rectangular patch with rounded corners to reduce waste.

Such drug delivery devices may also contain other permeation enhancers, stabilizers, dyes, diluents, pigments, carriers, inert fillers, antioxidants, excipients, gelling agents, anti-irritants, vasoconstrictors, as are known to the art.

According to one embodiment of a transdermal drug delivery device usable with this invention, the drug reservoir comprise 10–30 wt % drug and 68–80 wt % of an ethanol gel comprising 75–95% ethanol, 1–2 wt % of a gelling agent such as hydroxypropyl cellulose, and the remainder water; the rate control membrane comprises an ethylene vinyl acetate (EVA) copolymer having a vinyl VA content of 5–30 wt %, preferably 9–18%; and the adhesive comprises a PIB mixture comprising HMW PIB/LMW PIB/mineral oil in a ratio of 0.75–1.25/1–1.5/1.5–2.5, most preferably 1/1.25/2.

The aforementioned patents describe a wide variety of materials which can be used for fabricating the various layers and components of drug delivery devices usable according to this invention. This invention, therefore, contemplates the use of materials other than those specifically disclosed herein, including those which may hereafter become known to the art and to be capable of performing the necessary functions.

The following Examples are offered to illustrate the practice of the present invention and are not intended to limit the invention in any manner. Whether any particular adhesive formulation possesses the properties required according to this invention can be readily determined by following the simple procedure set forth in Example II.

EXAMPLE I

Testoderm® TTS transdermal delivery systems for the administration of testosterone over 24 hours through non-scrotal skin were made as follows. A reservoir gel comprising 26 wt % testosterone, 1–2 wt % hydroxypropyl cellulose, and the remainder 95% ethanol was prepared by mixing testosterone, 95% ethanol and adding hydroxypropyl cellulose with mixing. The testosterone gel loading was 21 mg/cm².

A PIB adhesive composition was made by mixing HMW PIB (MW 1200000), LMW PIB (MW 35000) and light mineral oil in a weight ratio of 1:1.25:2. A 50 micron thick layer of the PIB adhesive was cast onto a 75 micron thick film of siliconized polyethylene terephthalate release liner. The adhesive side of the resulting two layer subassembly was laminated to a 50 micron thick film of EVA (9% VA). The gelled testosterone-ethanol mixture was placed on the EVA membrane. A backing member comprised of aluminized polyethylene terephthalate with an EVA heat sealable coating was laid over the gels and heat-sealed to the EVA copolymer using a rotary heat seal machine. Finished systems were punched from laminate using a circular punch and placed in sealed pouches to prevent loss of volatile components. The device has been applied to non-scrotal skin of patients and thereafter removed and replaced without measureable decrease in adhesive/skin bond strength, such that the device remained on non-scrotal skin for the balance of the 24 hour administration period.

EXAMPLE II

A test sample of the PIB adhesive of Example I was obtained by removing the release liner and separating the EVA/PIB adhesive laminate from the backing member leaving a film of PIB adhesive on the EVA membrane. A silicone adhesive test sample was prepared by forming a film of H7-2292 amine resistant silicone adhesive available from Dow Corning on another 50 micron thick film of EVA (9% vinyl acetate).

Each EVA/adhesive strip was applied to the forearm of a subject. After a 20 minute dwell period, the strips were removed using an Instron machine to measure the force of removal. The force was approximately 95 gm/cm for the PIB adhesive and 195 gm/cm for the silicone adhesive.

The strips were then reapplied to the forearm of the subject. The silicone adhesive did not readhere to the subject while the PIB adhesive had approximately the same peel force upon subsequent removal (105 gm/cm). There was no evidence of delamination of the adhesive layer or contamination of the adhesive surface with the PIB adhesive sample whereas the adhesive properties of the silicone adhesive sample was essentially destroyed.

The invention has been described in detail with particular reference to certain preferred embodiments thereof, but it will be understood that variations and modifications can be affected within the scope and spirit of the invention.

We claim:

1. A method for transdermal administration of a drug through non-scrotal skin over a predetermined administration period comprising:
   a) placing a transdermal drug delivery device containing the drug and having an adhesive surface for maintaining the device on non-scrotal skin of an individual;
   b) removing said device from the skin prior to the expiration of said period; and
   c) reapplying said device on the non-scrotal skin of the individual;
   d) wherein said adhesive surface is formed from an adhesive formulation that provides (i) an initial adhesive/skin bond strength sufficient to maintain said transdermal drug delivery device on the non-scrotal skin to which it is applied for the entire predetermined administration period and (ii) an adhesive/skin bond strength upon replacement on non-scrotal skin sufficient to retain said device for the balance of said administration period.

2. The method of claim 1 wherein said initial bond strength is less than 195 gm/cm.

3. The method of claim 2 wherein the initial bond strength is at least about 95 gm/cm.

4. The method of claim 2 wherein said adhesive formulation is a non-cross-linked adhesive formulation.

5. The method of claim 4 wherein the non-cross-linked adhesive polymer is polyisobutylene (PIB).

6. The method according to claim 1 wherein the adhesive surface comprises a mixture of low molecular weight polyisobutylene (LMW PIB) and high molecular weight polyisobutylene (HMW PIB).

7. A method according to claim 6 wherein the low molecular weight polyisobutylene (LMW PIB) has a molecular weight of about 15,000–50,000 and the high molecular weight polyisobutylene (HMW PIB) has a molecular weight of about 990,000–1,6000,000.

8. A method according to claim 7 wherein the adhesive further comprises a plasticizer.

9. A method according to claim 8 wherein high molecular weight polyisobutylene (HMW PIB)/low molecular weight polyisobutylene (LMW PIB)/plasticizer ratio is: 0.75–1.25/1–1.5/1.5–2.5.

10. The method of claim 2 wherein the adhesive/skin bond strength on replacement is at least 72% of said initial bond strength.

11. The method of claim 10 when the adhesive/skin bond strength on replacement is at least 85% of said initial bond strength.

12. The method of claim 3 wherein said adhesive/skin bond strength on replacement is at least 72% of said initial bond strength.

13. The method of claim 12 wherein the adhesive/skin bond strength on replacement is at least 85% of said initial bond strength.

14. The method of claim 9 wherein the plasticizer is selected from the group consisting of mineral oil and polybutene.

15. The method of claim 1 wherein said drug is testosterone.

16. The method of claim 3 wherein said drug is testosterone.

17. The method of claim 13 wherein said drug is testosterone.

* * * * *